United States Patent [19]

Anderson et al.

[11] 4,006,169

[45] Feb. 1, 1977

[54] EPOXIDATION OF α,β-ETHYLENIC KETONES

[75] Inventors: Elvin L. Anderson, Moorestown, N.J.; Bing L. Lam, Haverford; George R. Wellman, Warminster, both of Pa.

[73] Assignee: SmithKline Corporation, Philadelphia, Pa.

[22] Filed: Feb. 26, 1976

[21] Appl. No.: 661,478

[52] U.S. Cl. ............................ 260/348 R; 424/278
[51] Int. Cl.$^2$ ...................................... C07D 303/32
[58] Field of Search ..................... 260/348 R, 348.6

[56] References Cited

UNITED STATES PATENTS 2,887,498  5/1959  Hearne et al. ................. 260/348.6

FOREIGN PATENTS OR APPLICATIONS 1,010,812  3/1952  France

OTHER PUBLICATIONS

S. Marmor, Jour. Org. Chem. (1963), pp. 250–251.

*Primary Examiner*—Norma S. Milestone
*Attorney, Agent, or Firm*—William H. Edgerton; Alan D. Lourie; Richard D. Foggio

[57] ABSTRACT

A method of preparing α,β-epoxy ketones by reacting water-soluble α,β-ethylenic ketones with sodium hypochlorite. Especially useful for preparing 3,4-epoxybutanone.

1 Claim, No Drawings

EPOXIDATION OF α,β-ETHYLENIC KETONES

This invention relates to a new method for epoxidation of certain α,β-ethylenic ketones.

The preparation of α,β-epoxy ketones from the corresponding ethylenic ketones has been limited in the prior art to direct epoxidation using a mild oxidizing agent, especially a peroxide, or to a two-step process involving formation of a halohydrin with subsequent cyclization using alkali. The unstable nature of ethylenic ketones makes the traditional methods of synthesizing α,β-epoxy ketones expensive, commercially impractical, or low yielding.

The use of peroxides for epoxidation has been described in U.S. Pat. No. 3,062,841 and the scientific publication corresponding to that patent, N. C. Yang et al., J. Am. Chem. Soc., 80:5845 (1958). The Yang method uses organic peroxides which are expensive to use in the commercial production of bulk chemicals. Also, Yang reports relatively long reaction times at his preferred temperatures which are 20° C. to 50° C. Yang also reports a 49% yield of a key and preferred product of this invention, 3,4-epoxybutanone. This yield is considerably lower than the yields obtained here — about 70%.

The two-step halohydrin reaction has, to the best of our knowledge, been applied sparingly to epoxidation of α,β-ethylene ketones except on a research basis. For example, P. Baret et al., C. A., 68:87075d reports using N-bromosuccinimide in a two-step process.

The epoxidation process of this invention has the advantage of using inexpensive inorganic oxidizing agents under reaction conditions in which the reaction proceeds quickly and in high yield. This process may be applied to any α,β-ethylenic ketone having no other interfering groups, such as those having centers susceptible to oxidation which are not desired to be affected. Also, the ethylenic ketones subject to this invention are only those which are substantially water-soluble, such as methyl vinyl ketone, mesityl oxide, ethylidene acetone or acrolein. A number of ethylenic ketones are mentioned in U.S. Pat. Nos. 3,062,841 and 2,246,032. Representatives of these compounds may be tested for water solubility by methods well-known in the art to ascertain whether they are susceptible to use in this new process. Of course, other vinyl groups present in the structure will be simultaneously oxidized as one skilled in the art will recognize.

The oxidizing agent in this reaction is a mixture of an alkali metal hypochlorite, preferably potassium or sodium hypochlorite, and hypochlorous acid, the latter formed by the equilibrium reached when a hypochlorite is dissolved in water. It is most often used in excess of stoichiometric quantities. Especially useful are the commercially available laundry bleach products which contain about 5% sodium hypochlorite in water. The reaction media are aqueous in th pH range of about 8.0–8.5 which range must be maintained during the reaction, such as by addition of mineral acid such as dilute hydrochloric or sulfuric acid. When the reaction mixture is too basic, yields are lower and polymeric side products are formed. At too acid pH's polyhalo compounds are obtained, especially at a pH of about 5. Therefore, most advantageous results are obtained within the given preferred pH range.

The reaction temperature is material for best yields with most advantageous results being obtained at from about −15° C. to +20 C., preferably about 0° C. to 10° C. The reaction time is not critical but the reaction usually proceeds exothermally in a few minutes, say up to about 5 minutes. Longer reaction times may be used when less than advantageous conditions are present or when a slightly soluble α,β-ethylene ketone is the starting material so that only a small amount of reaction takes place at any one time, i.e., in a continuous type of reactor.

The desired reaction product is isolated as known to the art. For example, the reaction mixture is acidified to pH 7, extracted with an immiscible organic solvent such as methylene chloride then the product is isolated therefrom by distillation or crystallization.

The yields of this reaction usually run from 50–70% of theoretical and give very pure product under the most advantageous conditions described herein.

The end product epoxy ketones are useful intermediates for preparing other compounds having various medicinal activities. Also, they may be used per se in forming resinous polyesters or polyethers as described in U.S. Pat. No. 3,062,841, column 8.

During the reaction of the preferred methyl vinyl ketone, as described in Example 1, a particularly useful byproduct was isolated which to the best of our knowledge is a novel chemical. This compound, 1,1,1-trichloro-3,4-epoxy-2-butanone, and its hydrate are active in inhibiting microbial deamination in ruminants (79% inhibition at 25 p.p.m.) by tests described in U.S. Pat. No. 3,862,333. The hydrate form, 1,1,1-trichloro-2,2-dihydroxy-3,4-epoxy butane, has activity in vitro against Candida albicans at about 12.5 μg./ml.

The following example will illustrate this invention. Variations of the synthetic process or applications to other starting materials will be obvious to those skilled in the art.

EXAMPLE 1

A 5% solution of sodium hypochlorite in water (Clorox TM, 800 ml.) is cooled to −10° C. and partially neutralized with hydrochloric acid to pH 8–8.5. Undistilled methyl vinyl ketone (31 ml., 26 g., 0.37 m.) is added in one portion causing an exotherm which is controlled by external cooling. The pH begins to rise and hydrochloric acid is added dropwise to maintain a pH of 8–9. After 3–5 minutes, the pH of the reaction mixture is adjusted to 7.2. It is then extracted with methylene chloride (3 × 500 ml.). The organic extracts are combined, dried over magnesium sulfate and concentrated to ~ 40 ml. by atmospheric distillation through a 300 mm. air-cooled column. The residue is vacuum distilled and the fractions boiling at 60°–80° C. (60 torr) are collected. The appropriate fractions (conveniently determined by G.L.C. using 5% OV-225 on 6 feet × 1/4 inch glass column at 80° C.) are combined to give 22.3 g. (70%) of 3,4-epoxybutanone, 95% pure by G.L.C., $n_d^{22°}$ 1.4250 (lit. 1.4228).

The fraction boiling at 80°–90° C. (10 torr) gives 4.8 g. (7%) crude 1,1,1-trichloro-3,4-epoxybutanone. Redistillation gives an analytically pure sample of product, $n_d^{21°}$ 1.4905, m.p. 18°–19° C..

| $C_4H_3Cl_3O_2$ | | C 25.36 | H 1.60 | Cl 56.15 |
|---|---|---|---|---|
| | calc. | | | |
| | found | 25.39 | 1.78 | 56.48 |

H'-N.M.R. (CDCL$_3$, IMS): δ = 3.14 (m,2), 4.43 (m,1).

Dissolution of 1,1,1-trichloro-3,4-epoxybutanone (6.0 g., 0.319 m) in hot water (12 ml.) gives on cooling, 5.7 g. (85%) of its hydrate, m.p. 92°–95° C.

| $C_4H_5Cl_3O_3$ | calc. | C 23.16 | H 2.43 | Cl 51.27 |
|---|---|---|---|---|
| | found | 22.88 | 2.42 | 51.21 |

Stoichiometric quantities of any substantially water-soluble $\alpha,\beta$-ethylenic ketone, such as mesityl oxide, ethylidene acetone, etc., may be substituted in the above reaction.

What is claimed is:

1. 1,1,1 Trichloro-3,4-epoxy-2-butanone and its hydrate said hydrate being 1,1,1-trichloro-2,2-dihydroxy-3,4-epoxybutane.

\* \* \* \* \*